(12) United States Patent
Müller et al.

(10) Patent No.: US 9,826,926 B2
(45) Date of Patent: Nov. 28, 2017

(54) IMPLANTABLE SENSOR ELEMENT

(75) Inventors: Achim Müller, Grossostheim (DE);
Peter Herbrechtsmeier, Königstein (DE)

(73) Assignee: EyeSense AG, Basel (CH)

( * ) Notice: Subject to any disclaimer, the term of this patent is extended or adjusted under 35 U.S.C. 154(b) by 1956 days.

(21) Appl. No.: 13/122,087

(22) PCT Filed: Oct. 2, 2009

(86) PCT No.: PCT/EP2009/062823
§ 371 (c)(1),
(2), (4) Date: May 31, 2011

(87) PCT Pub. No.: WO2010/037847
PCT Pub. Date: Apr. 8, 2010

(65) Prior Publication Data
US 2011/0224514 A1   Sep. 15, 2011

(30) Foreign Application Priority Data
Oct. 2, 2008   (EP) .................................... 08165703

(51) Int. Cl.
*A61B 5/1455*   (2006.01)
*A61B 5/1459*   (2006.01)
(Continued)

(52) U.S. Cl.
CPC ........ *A61B 5/1459* (2013.01); *A61B 5/14546* (2013.01); *A61B 5/14735* (2013.01);
(Continued)

(58) Field of Classification Search
USPC ................................................ 600/310–344
See application file for complete search history.

(56) References Cited

U.S. PATENT DOCUMENTS

| 4,582,809 A | 4/1986 | Block et al. |
| 4,842,783 A | 6/1989 | Blaylock |

(Continued)

FOREIGN PATENT DOCUMENTS

| EP | 0340105 | 11/1989 |
| EP | 1810665 | 7/2007 |
| WO | WO-96/24074 | 8/1996 |
| WO | WO-01/13783 | 3/2001 |
| WO | WO-02/30275 | 4/2002 |
| WO | WO-02/087429 | 11/2002 |
| WO | WO-2005/054831 | 6/2005 |
| WO | WO-2005/079970 | 9/2005 |

OTHER PUBLICATIONS

European Search Report dated Mar. 4, 2009, 2 pgs.
PCT IPRP in PCT/EP2009/062823, dated Dec. 4, 2009, 8 pgs.

*Primary Examiner* — Eric Winakur
*Assistant Examiner* — Marjan Fardanesh
(74) *Attorney, Agent, or Firm* — Servilla Whitney LLC

(57) ABSTRACT

The invention relates to a sensor element for detecting at least one analyte in a body fluid or in a body tissue, particularly for determining at least one metabolite concentration in a body fluid. The sensor element comprises an implantable, one-piece shaped body, which comprises a sensor end and a coupling end. The shaped body comprises, in the area of the sensor end, at least one sensor area, which comprises at least one sensor material. The sensor material changes at least one optically measurable property in the presence of the analyte. The shaped body also has at least one optically transparent coupling part, which is designed to transmit electromagnetic radiation in at least one spectral range between the sensor area and the coupling end. In the sensor area, the shaped body has at least one optically transparent matrix material, and the analyte can at least partially diffuse through the matrix material to the sensor material. The sensor material is embedded in the matrix material. The coupling part is formed at least partially by the matrix material.

21 Claims, 3 Drawing Sheets

(51) Int. Cl.
- *A61B 5/1473* (2006.01)
- *B29C 39/00* (2006.01)
- *B29C 39/02* (2006.01)
- *B29C 39/10* (2006.01)
- *A61B 5/145* (2006.01)
- *A61B 5/00* (2006.01)
- *B29C 39/24* (2006.01)

(52) U.S. Cl.
CPC .......... *B29C 39/006* (2013.01); *B29C 39/021* (2013.01); *B29C 39/025* (2013.01); *B29C 39/10* (2013.01); *A61B 5/14532* (2013.01); *A61B 5/685* (2013.01); *A61B 2562/0238* (2013.01); *A61B 2562/12* (2013.01); *B29C 39/023* (2013.01); *B29C 39/028* (2013.01); *B29C 39/24* (2013.01)

(56) References Cited

U.S. PATENT DOCUMENTS

| | | | |
|---|---|---|---|
| 5,353,792 A * | 10/1994 | Lubbers et al. | 600/311 |
| 5,508,317 A | 4/1996 | Muller | |
| 6,256,522 B1 | 7/2001 | Schultz | |
| 7,226,414 B2 | 6/2007 | Ballerstadt et al. | |
| 2002/0058863 A1 * | 5/2002 | Petersson et al. | 600/310 |
| 2006/0024357 A1 | 2/2006 | Carpenter et al. | |
| 2007/0122829 A1 | 5/2007 | Ballerstadt et al. | |

* cited by examiner

IMPLANTABLE SENSOR ELEMENT

BACKGROUND

The invention relates to a sensor element for detecting at least one analyte in a body fluid or in a body tissue. The invention further relates to a sensor arrangement which comprises a sensor element according to the invention and an optical detector. The invention also relates to a method for generating a sensor element. Such sensor elements, sensor arrangements and methods are used in particular for determining at least one metabolite concentration in a body fluid and/or in a body tissue. Such metabolites can include by way of example, but not exclusively, blood glucose, lactate, cholesterol or other types of analytes and metabolites. Alternatively or in addition, however, the sensor element or the sensor arrangement can also be used in other fields of analysis, for example in the field of analytical chemistry, particularly in in situ analysis, process monitoring or in similar fields.

Conventional systems for determining analyte or metabolite concentrations are in many cases based on generating a sample of a body fluid, for example a drop of blood, which is then tested with respect to its analyte content by means of a suitable measurement appliance. For example, optical and/or electrochemical measurement methods can be used.

In order to reduce the inconvenience that patients experience in connection with the frequent generation of blood samples, various non-invasive or minimally invasive techniques have been developed for measuring analyte concentrations. Determination of the blood glucose concentration is discussed below without limiting the scope of protection of the invention, as it is of course also possible, alternatively or in addition to this, to detect other types of analytes and metabolites.

The invasive techniques for determining the analyte concentration are usually based on sensors which can be implanted into a body tissue and/or into a body fluid and which can determine the analyte concentration by optical and/or electrochemical means.

Optical systems generally use at least one sensor material which changes at least one optically measurable property in the presence of one or more specific analytes. This optically measurable property can take the most diverse forms, with many different methods, sensor materials and measurement devices being known from the prior art. In principle, all of these known sensor materials can also be used in the context of the present invention.

Thus, for example, WO 01/13783 describes an ocular sensor for glucose, which is designed as an ophthalmic lens. The ocular sensor comprises, as sensor material, a glucose receptor, which is marked with a first fluorescence label, and a glucose competitor, which is marked with a second fluorescence label ("donor"). The two fluorescence labels are chosen such that, when the competitor is bound to the receptor, the fluorescence of the second fluorescence label is quenched on account of a resonant fluorescence energy transfer. By monitoring the change in the fluorescence intensity at a wavelength around the fluorescence maximum of the quenchable fluorescence label, it is possible to measure the proportion of the fluorescence-marked competitor that has been displaced by the glucose. In this way, the glucose concentration in the eye fluid can be determined. The measurement can in turn be used to draw conclusions regarding the blood glucose concentration. Other types of detection are also conceivable and are familiar to persons skilled in the art, for example a fluorescence detection of the first fluorescence label.

WO 02/087429 describes a fluorescence photometer by means of which blood glucose concentrations can be determined by measuring the glucose concentrations from the eye fluid. The illustrated device is able to measure simultaneously two fluorescence intensities at different wavelengths.

However, a challenge that arises when using optical detection systems based on an optical sensor material in implanted sensors is of course that of conducting optical signals from a measuring appliance to the sensor material and/or in the reverse direction, i.e. from the sensor material to the measuring appliance. In the devices described in WO 01/13783 and WO 02/087429, this problem is of lesser importance, since the tissue layers that cover the implanted sensor are generally transparent in the region of the eye and thus permit coupling in and out of light signals. However, the technical challenge of optical coupling increases when sensors are implanted in non-transparent skin areas. The present invention is therefore not limited to use in the eye region and instead also includes the possibility of implantation in areas of the body where the implanted sensor is covered by non-transparent tissue parts.

To overcome the described problems of optical coupling, various systems are known from the prior art. Thus, for example, WO 2005/054831 A1 describes a sensor element for determining a glucose concentration, which uses an optical waveguide. A sensor element is applied to the distal end of the optical waveguide, which sensor element comprises a binding protein that can bind with at least one target analyte. The sensor element furthermore comprises at least one reporter group which is subject to a change in luminescence if the analyte concentrations change. The sensor element optionally comprises reference groups with luminescence properties that do not substantially change if the analyte concentrations change.

D. Meadows and J. S. Schultz: Fiber-optic biosensors based on fluorescence energy transfer, Talanta, vol. 35, no. 2, pages 145-150, 1988, describe a biochemical glucose-testing method based on a fluorescence energy transfer. Among other things, they propose the use of optical waveguides for coupling to a sensor element. The sensor element comprises a hollow dialysis fiber through which the analyte to be detected, in this case glucose, is able to diffuse and thus reach the sensor material located in the inside of the dialysis fiber.

U.S. Pat. No. 7,226,414 B2 describes a glucose sensor device to be implanted within the subcutaneous tissue of an animal body. A sensor material is arranged in a first chamber, with glucose being able to enter the first chamber from the body tissue. The sensor element further comprises a reference chamber with a reference solution. The use of optical waveguide fibers that connect a detection appliance to the chambers is once again proposed for coupling a read-out appliance thereto.

US 2007/0122829 A1 proposes a system, a device and a method for measuring the concentration of an analyte in a liquid or a matrix. A thermodynamically stabilized, analyte-binding ligand is proposed. In this case too, the use of a separate optical waveguide, which is in the form of a fiber and coupled to a sensor element, is again proposed, which optical waveguide connects a detection appliance to an implanted sensor element.

However, aside from the disclosed sensor materials, which can also be used for example in the context of the present invention, WO 2005/054831 A1, the publication by D. Meadows et al., U.S. Pat. No. 7,226,414 B2 and US 2007/0122829 A1 have considerable disadvantages in practice. One considerable disadvantage lies in the expensive production of such sensor elements, since the actual sensor element itself first has to be produced, after which it has to be connected to a suitable optical waveguide fiber, in order subsequently to implant this arrangement. Since optical waveguide fibers in practice have considerable sensitivity to mechanical loads, it can also happen that the optical waveguides are damaged during implantation, as a result of which the functionality of the sensor elements is adversely affected or indeed prevented. Moreover, in order to remove the sensor elements, including the optical fibers, it is sometimes necessary to perform considerable interventions in the body tissue, since pulling the optical waveguide fibers out of the body tissue generally causes detachment of the sensor element from the optical waveguide fiberfiber.

SUMMARY

Embodiments of the present invention provide a sensor element and a method for the production thereof, which sensor element and method avoid one or more of the above-described disadvantages of known sensor elements and methods. In particular embodiments, the sensor element should permit reliable and mechanically stable coupling of an optical detector, while according to certain embodiments, a further aim is at the same time to ensure implantation that is quick and causes the least possible pain.

According to one embodiment, a sensor element for detecting at least one analyte in a body fluid or in a body tissue is proposed which can in particular be used to determine at least one metabolite concentration in a body fluid. For possible examples of analytes, reference can be made to the above description of the prior art. The term "detecting" can in this case be understood as meaning a quantitative and/or qualitative determination of an analyte concentration, i.e. a determination of the amount and/or concentration of the analyte in the body fluid and/or the response to the question of whether the analyte is in fact contained at all in the body fluid.

In one embodiment, the sensor element comprises an implantable, one-piece shaped body. The term "implantable" is to be understood as meaning that the shaped body is made substantially of biocompatible materials and/or has a biocompatible coating, such that this shaped body can remain implanted in a body tissue over an extended period (for example for several days and/or weeks), without rejection reactions and/or inflammations and/or poisoning of the body tissue. The term "one-piece" is to be understood as meaning that the shaped body is designed substantially as an individual shaped part which does not divide up into a plurality of parts even under mechanical loading (for example the compressive and/or tensile loads that usually occur when implanting the sensor element or when removing it from the body tissue). In particular, the term "one-piece" can also entail that the shaped part can be produced in a single work step. In particular, as is described below, a sensor area and a coupling part should not detach from each other under such loads.

The shaped body can in particular embodiments be of an overall elongate design, i.e. a design with a length that is greater than the diameter of the shaped body. For example, the shaped body can have a cylindrical design with a round or polygonal cross section. Overall, the shaped body should have a length that corresponds at least approximately to the sum thickness of dermis and epidermis, such that the sensor end of the implanted sensor element is arranged in the lower dermis layers or in the layers of the subcutis, in order to detect the analyte there.

According to one or more embodiments, the sensor area comprises at least one sensor material which changes at least one optically measurable property in the presence of the analyte. The sensor material is configured such that this sensor reacts sensitively to the at least one analyte to be detected. This sensor property is preferably specific to the analyte that is to be detected. Various detection principles can be used. For example, the analyte can react chemically with the sensor material (for example by a covalent bond, complex bond or a similar connection), which bond can be detected, for example, by a change in fluorescence properties and/or colour properties of the analyte and/or of the sensor material and/or of the combination of sensor material and analyte. Looser bonds are also possible, for example physical bonds and/or approximation of sensor material and analyte, which in turn can be detected spectroscopically. In any case, however, the sensor material is configured in such a way that at least one optically detectable physical and/or chemical property of the implant changes when the analyte concentration changes in the environment of the sensor element or when an analyte is present in the environment of the sensor element.

To couple light into and out of the sensor area, the shaped body also has at least one optically transparent coupling part. This coupling part, which is spatially separate from the sensor area but in one piece with the latter to form a shaped part, is designed to transmit electromagnetic radiation in at least one spectral range between the sensor area and the coupling end. In contrast to the optical waveguide fibers and by means of which light is coupled to the implanted sensor elements, it is thus proposed, in the context of embodiments of the present invention, that the coupling part be connected in one piece to the sensor area. This ensures increased mechanical stability since, particularly at the connection point between coupling part and sensor area, there are no longer any connections that can come loose under tensile loads and that could lead to destruction of the sensor element upon implantation of the sensor element or removal thereof from tissue.

Moreover, the coupling part does not necessarily have to be designed as an "optical waveguide" in the traditional sense, and instead it can simply constitute a "window", for example, permitting optical coupling to the sensor area. In the implanted state, the coupling end of the coupling part can still be arranged below the uppermost layer of skin, such that optical coupling can take place through this uppermost layer of skin which is still substantially transparent (at least in the visible, infrared and/or ultraviolet spectral range). It is possible to largely dispense with optical waveguide properties, in particular the properties of optical waveguides with core and shell for adapting the refractive index, or graded-index fibers.

This integrality between shaped body and sensor area is achieved, according to embodiments of the invention, by virtue of the shaped body having, in the sensor area, at least one optically transparent matrix material. The matrix material is chosen such that the at least one analyte to be detected can diffuse at least partially through the matrix material to the sensor material embedded in the matrix material. At the same time, however, the coupling part is also at least partially formed by the matrix material. The above-described integrality of the shaped body is ensured in this way, since the sensor area and the coupling part now differ from each other only in that the sensor material is embedded in the sensor area, whereas the coupling part is preferably substantially free of sensor material.

A matrix material can be understood here as meaning a single-phase material, that is to say a material that has both macroscopically and also microscopically homogeneous properties, for example a material that has a single principal element in crosslinked form. Alternatively, however, the matrix material can also be configured as a multiple-phase material, that is to say as a material which, for example, is substantially homogeneous at the macroscopic level but has several phases at the microscopic level. As an example of a microscopically heterogeneous, multiple-phase system, mention may be made of silicone hydrogels, in which the hydrogel phase is only one of several phases present alongside one another. Alternatively or in addition, however, other matrix materials can also be used, for example random copolymers, that is to say copolymers in which two or more different principal elements follow each other in random sequence. Random polymers of this kind also usually form homogeneous phases.

The coupling part and the sensor area can be produced in particular by at least substantially simultaneous curing of the matrix material and/or of a precursor of the matrix material in the sensor area and in the area of the coupling part. A precursor is to be understood as any desired starting product or intermediate product which by itself, or together with other substances, can form the matrix material by chemical reaction or also by a phase transition. The sensor material can be immobilized in the matrix material in particular by suitable embedding and/or by chemical bonding, in order to avoid diffusion of the sensor material into surrounding body tissue, at least for the periods during which the sensor element is normally implanted in the body tissue. In particular, the sensor element can be at least partially embedded in microparticles or nanoparticles, particularly in microcapsules or nanocapsules.

It is also preferable if the matrix material in the sensor area, in the implanted state of the sensor element, is in direct contact with the body fluid and/or the body tissue. To this end, it is possible in particular to dispense with encasing the matrix material in the area of the sensor element. It is also possible to dispense with expensive membranes, for example the dialysis membranes known from the prior art.

As has been described above, the coupling part can be designed in particular as an elongate coupling part with a substantially homogeneous refractive index. "Elongate" can be understood here as meaning a ratio between length and diameter of a factor of at least 2, preferably 5, and particularly preferably ca. 10 or more. The diameter can, for example, be in the range of between 100 micrometers and 1 millimeter, in particular in the range of between 200 micrometers and 500 micrometers. The length can, for example, be in the range of between 1 and 8 millimeters, preferably in the range of between 2 and 5 millimeters. The ratio between diameter and length is preferably in the range of between 1:5 and 1:20, in particular ca. 1:10. The exact sizes and dimensions of the sensor element can in particular also be adapted to the site of implantation of the sensor element.

The matrix material can comprise at least one crosslinkable plastic, in particular a biocompatible crosslinkable plastic, in crosslinked form. The crosslinkable plastic can preferably comprise a hydrogel, since this material has already proven in many situations to have good processing qualities and excellent biocompatibility, particularly in the field of eye implants. Alternatively or in addition, however, it is also possible and advantageous to use a polymethyl methacrylate and/or a polycarbonate and/or a polystyrene and/or a silicone, or combinations of said materials and/or of other materials.

The crosslinkable plastic can in particular be produced using at least one nelfilcon polymer. Polymers of this kind are set forth, for example, in EP 807 265 B1 or in EP 790 258 B1. These are crosslinkable or crosslinked polyvinyl acetates or a crosslinkable derivative of the polyvinyl acetate, crosslinkable polyvinyl alcohols or a crosslinkable derivative of the polyvinyl alcohol. It is also possible to use crosslinkable polymers based on polyethylene glycol, in particular based on at least one of the following polymers: bis(acryloyl) polyethylene glycol, bis(acrylamido) polyethylene glycol, a polyurethane based on polyethylene glycol, a bis- or tris-isocyanate, an acryloyl isocyanate, a crosslinkable polymer based on crosslinkable silicone hydrogel copolymers, in particular based on co-polycondenates of bis (aminodimethyl) siloxanes and/or hydrophilic di- and/or tri-isocyanates and/or acryloyl isocyanates. Alternatively or in addition, it is also possible to use telechelic polymers (telecheles) and/or multivalent hydrophilic polymers, that is to say hydrophilic polymers with crosslinkable end groups, for example acryl and/or acrylamide groups. Examples of hydrophilic starting monomers are one or more of the following monomer units: vinyl pyrrolidone, hydroxyethyl methacrylate, hydroxyethyl acrylate, dimethylacrylamide, acrylamide, acrylic acid. Telecheles and multivalent polymers can be produced, for example, by the customary live polymerizations or by use of functional chain transfer reagents.

As has been explained above, it is particularly preferable if the shaped body is in direct contact with the body tissue. This means that it is possible to dispense with encasing the shaped body, particularly in the sensor area and/or also in the area of the coupling element. If necessary, however, the shaped body can still be provided with a coating, in particular with a biocompatible coating. For this purpose, a multilayer coating (for example using a layer-by-layer method) and/or a plasma coating can be used in particular.

Since the shaped body is implanted in a body tissue, the shaped body can also comprise at least one active substance that promotes healing. This active substance that promotes healing can in turn be arranged in a coating around the shaped body and/or in the shaped body itself. The active substance that promotes healing should be arranged in and/or on the shaped body in such a way as to be able to diffuse into the surrounding body tissue, so as to accelerate the healing there. The active substance that promotes healing can, for example, be a cortisone and/or a cortisone derivative, in particular dexamethasone. However, other active substances that promote healing can of course also be used. The active substance that promotes healing can in particular ensure that, after implantation, a completely closed layer of tissue quickly forms over the sensor element, in contrast to conventional sensor elements which generally protrude from the tissue layers.

The sensor element is designed such that a part of the shaped body is designed as a sensor area, whereas the other part, namely the coupling element, can serve as a transparent "window" for optical measurement of a sensor signal. When used under the skin, biosensors whose analyte-specific change is read out by optical measurements often have the particular disadvantage that the skin absorbs very strongly in the range of the visible spectrum and, in addition, has strongly diffuse scattering. The absorption and scattering lead to considerable losses of intensity and to artefacts, the source of which lies in the changing scattering behaviour of the skin. Both effects mean that it is difficult to obtain precise measurements with optical sensors under the skin. Another difficulty is that sensors for measuring metabolites under the skin usually have to be implanted in relatively deep layers of skin in which there is good circulation of blood. For this reason, however, use in the uppermost layers of the skin is not possible.

By contrast, in the sensor element according to the invention, a "layer structure" is used in which the sensor area can be arranged in deep layers of the skin. The coupling part which lies above this, and which does not have to be an optical waveguide in the traditional sense, simply serves to form an optically transparent "window" to the skin surface or to close under the skin surface. This transparent part of the coupling part provides for uninfluenced conduction of the light. Unlike a traditional waveguide, this coupling part does not necessarily need to have a core with a high refractive index and a shell with a lower refractive index, and instead can be a homogeneous transparent material. A shell/core structure is not necessary because of the short length of the implant.

In the sensor area, one or more reference materials can also be embedded in the matrix material in addition to the at least one sensor material. These can, in particular, be reference particles, although other types of reference materials are also possible, for example reference molecules or the like. This reference material should be chosen such that it has at least one optically measurable property (for example once again a luminescence and/or fluorescence property, a colour or the like), which does not substantially change even in the presence of the at least one analyte. It is thus possible for example, by measuring the optical property of the reference material, to perform calibrations and/or compensation measurements in order, for example, to eliminate intensity fluctuations of a light source and/or environmental influences acting on the skin areas during the measurement. The reference material can, for example, be immobilized in the matrix material. The reference material can, for example, once again be incorporated into the matrix material in the form of microparticles or nanoparticles, in the form of microcapsules or nanocapsules and/or chemically bonded to the matrix material.

The sensor element in one of the embodiments described above can be used in particular in the context of a sensor arrangement according to the invention. Such a sensor arrangement comprises at least one sensor element according to one or more of the above-described embodiments. The sensor arrangement further comprises at least one optical detector, wherein the detector is designed for coupling optically to the coupling end of the sensor element, when the sensor element is implanted in a body tissue, and for measuring the at least one optically measurable property of the sensor material.

For this purpose, the detector can, for example, comprise a detector for electromagnetic radiation, for example a photodiode, a photoelectric cell, or another type of detector for electromagnetic radiation. Moreover, one or more devices for spectral separation can be provided, for example gratings, filters, dichroitic mirrors or similar means. Depending on what optical property of the sensor material and/or of the reference material is to be detected, the sensor arrangement can include, in addition to a detector of this type, also a radiation source for generating electromagnetic radiation and for coupling this radiation into the coupling end of the sensor element. For this purpose, it is possible, for example, to provide light-emitting diodes, incandescent lamps, gas discharge lamps or other types of light sources. In this way, for example, fluorescence and/or luminescence can be excited in the sensor material and/or in the reference material. If only a colour change is measured, it is alternatively or additionally possible to dispense with the irradiation of excitation light. Moreover, optionally separate detectors and/or separate light sources can be provided for measuring the reference material, such that the optical property of the sensor material and the optical property of the reference material can be detected separately. It is also possible, however, to partially or completely combine the components necessary for the measurement.

As has been described above, and in contrast to the sensor arrangements which are known from the prior art and which use optical waveguide fibers, it is not necessary for the coupling part of the proposed sensor element to be coupled directly to the optical detector or to a detection device that accommodates the optical detector and/or one or more sources. Thus, the optical detector and the sensor element, or the coupling end of the sensor element, can be separated from each other by at least one layer of skin or layer of tissue. The coupling part merely provides a wide "window" through which the sensor area can be "viewed". A slight covering of the surface of the sensor element by tissue is possible, in contrast to optical waveguide fibers.

The sensor arrangement can thus be constructed such that it includes, in spatially separate form, the sensor element and the detector, or a detection device comprising the detector and if appropriate one or more radiation sources. Moreover, additional elements can be provided, particularly inside the detection device, for example elements for evaluating the measurement, such as one or more input and output elements, one or more data processing devices (for example microprocessors), volatile and/or non-volatile memories, or further elements. It is also possible to provide one or more energy supplies and/or means for coupling an external energy supply to the detection device.

In addition to the above-described sensor element and the sensor arrangement in one of the described embodiments, a method is also proposed for producing a sensor element for detecting at least one analyte in a body fluid or in a body tissue. In particular, the proposed method can be used in order to produce a sensor element according to one of the above-described embodiments, such that reference can largely be made to the above description for possible definitions and preferred embodiments of the sensor element.

In the method according to embodiments of the invention, a first prepolymer liquid with at least one first curable prepolymer for producing an optically transparent coupling part is introduced into a cannula. A "prepolymer liquid" is to be understood as meaning any desired liquid (i.e. for example a solution and/or emulsion and/or suspension) which can be cured by a chemical reaction and/or a phase change. For example, the prepolymer liquid can comprise the above-described at least one precursor, and the prepolymer liquids can comprise different or identical precursors. Here, "curing" is to be understood as meaning a change from a liquid state to a solid state, although this change can also be effected only partially, with the result that a certain degree of deformability of the cured prepolymer can still remain after curing. The curing process can, in particular, be initiated by, for example, thermal, chemical, photochemical or other types of initiation.

Moreover, a second prepolymer liquid with at least one second curable prepolymer for producing a sensor area is introduced into the cannula. This method step can be carried out before or after or at the same time as the above-described method step of introducing the first prepolymer liquid. The second prepolymer liquid can be different than the first prepolymer liquid, although it can also be entirely or partially identical to the first prepolymer liquid. In the latter case, the method steps for introducing the prepolymer liquids into the cannula can also be combined into a single method step. However, it is then necessary to separately introduce the sensor material into the second prepolymer liquid, or into that area of the prepolymer liquid forming the sensor area, for example by subsequent inward diffusion. In this case, the "first" prepolymer liquid and the "second" prepolymer liquid differ from each other only subsequently in terms of their function, namely after the coupling part and the sensor area are formed.

Moreover, at least one sensor material is introduced into the second prepolymer liquid, wherein the sensor material changes at least one optically measurable property in the presence of the analyte. The introduction of the sensor material can take place before or after the introduction of the prepolymer liquid into the cannula. Thus, for example, the sensor material can be introduced before the second prepolymer liquid is forced and/or sucked into the cannula and/or the sensor material can also be introduced into the second prepolymer liquid, for example by inward diffusion, only afterwards, i.e. after the second prepolymer liquid is already situated in the cannula. For possible embodiments of the sensor material, reference can largely be made to the above description.

Thereafter, the first prepolymer liquid and the second prepolymer liquid are crosslinked, such that a shaped body with a sensor end and a coupling end is obtained.

For possible embodiments of the prepolymer liquid, reference can largely be made to the above description, such that the above-described crosslinkable plastics or materials in particular can be used for the first prepolymer and the second prepolymer. As has been explained above, it is particularly preferable to use hydrogel, since hydrogel shaped bodies can be produced particularly easily by successive drawing of prepolymer solutions into a suitable cannula. Because of the high viscosity and the small cannula cross section, the two prepolymer solutions do not mix together, and, in the cannula, the prepolymer solutions for the coupling part and for the sensor area preferably lie in layers and separate from each other. The prepolymer liquids can now be crosslinked in the cannula (for example photochemically in a glass cannula and/or thermally, for example in a steel cannula) and then injected with the cannula into the skin. This injection can be effected, for example, by inserting the cannula into an area of skin, after which, upon slow withdrawal of the cannula from the area of skin, the implant is forced out of the cannula. An alternative solution is to cure the prepolymer liquids directly upon injection, for example by use of UV light. Generally, the curing or crosslinking can be done photochemically, in particular by UV light, thermally, or in some other way.

As has been described above, suitable materials for the first and/or second prepolymer liquid are in particular a nelfilcon polymer, a crosslinkable polyvinyl acetate or a crosslinkable derivative of the polyvinyl acetate, a crosslinkable polyvinyl alcohol or a crosslinkable derivative of the polyvinyl alcohol. Examples of crosslinkable PVA derivatives of this kind are set forth in EP 641 806 B1, EP 790 258 B1 or EP 807 265 B1. It is also possible to use other crosslinkable prepolymers, for example based on polyethylene glycol (for example bis(acryloyl) PEG, bis(acrylamido) PEG, polyurethanes based on PEG, bis- or tris-isocyanates, and acryloyl isocyanates) or based on crosslinkable silicone hydrogel copolymers (co-polycondenates of bis(aminodimethyl) siloxanes and hydrophilic di- or tri-isocyanates and acryloyl isocyanates). A mixture of various prepolymers is also possible for the transparent part and sensor part.

It is particularly preferable if the first curable prepolymer and the second curable prepolymer are at least partially chemically identical and in particular comprise a common curable matrix material. In this way, in particular, the above-described sensor elements can be produced with the common matrix material for the transparent coupling part and the sensor area. However, embodiments with different prepolymers or matrix materials for coupling part and sensor area can also be produced by means of the proposed method.

The shaped body can at least partially correspond, in terms of its outer shape, to the shape of the inner lumen of the cannula, particularly in the cured state. This can be achieved in particular by the curing taking place entirely or partially within the cannula, for example within a transparent cannula in the case of photochemical curing (for example UV irradiation) or within a thermally conductive cannula (for example a steel cannula) in the case of thermal initiation of the curing process. In this way, the curing can be associated at the same time with a shaping process. The crosslinking or curing can take place entirely or partially within and/or outside the cannula.

Various techniques can be used to introduce the prepolymer liquids into the cannula. For example, the prepolymer liquids can be introduced into the cannula from at least one prepolymer reservoir, in particular by being sucked in by means of an underpressure and/or by being forced in by means of an overpressure.

It will be noted that a "cannula", in the context of the present invention, is to be understood as a substantially tubular structure which has an inner lumen. This inner lumen can have a constant and/or variable cross section. Instead of a single inner lumen, however, it is also possible for cannulas to be used that have several inner lumens, such that it is also possible, for example, to produce multi-layered sensor elements. Thus, the cannula can, for example, comprise several lumens which are arranged around each other in a ring shape and in which, for example, different prepolymer liquids can be accommodated. Contiguous arrangements of several ring-shaped lumens are also conceivable.

As has been described above, the use of hydrogel materials is particularly preferred, since such materials have particularly good biocompatibility and in particular can also be used without a coating. However, it is also possible to additionally provide a coating. Such a coating can comprise, for example, at least one of the following coatings:
   a biocompatible coating, in particular a hydrogel coating;
   a multi-layer coating;
   a coating with at least one active substance that promotes healing;
   a coating with at least one second sensor material that changes at least one optically measurable property in the presence of the analyte.

Coatings of these kinds can be applied by various methods. Particular preference is given to immersion methods, in particular immersion methods with a subsequent crosslinking step in order to crosslink the coating, co-extrusion methods by means of a cannula with at least two extrusion lumens, wherein at least a first of the extrusion lumens is used to generate the coating and at least a second of the extrusion lumens is used to generate the coupling part and/or the sensor area. However, other methods for generating the coating are also conceivable, for example immersion methods in a layer-by-layer technique and/or plasma coatings. Moreover, at least one preliminary treatment step can be performed prior to the application of the coating, in order to improve the adherence of the coating to the shaped body, for example a chemical, thermal or photochemical pretreatment.

In addition to the sensor element and the method for producing a sensor element, the invention also relates to a device for generating a sensor element. The device can be used in particular to generate a sensor element according to one or more of the above-described illustrative embodiments, such that reference can once again largely be made to the above description and to the above possible configurations. The device is designed to carry out a method according to one of the preceding method claims. For this purpose, the device has means for carrying out the individual method steps. The individual methods steps can be performed manually and/or also partially or completely automatically.

The device can be designed in particular not only to produce the sensor element but also to implant the latter in a body fluid and/or a body tissue. For this purpose, the device has at least one cannula for penetrating a skin area of a patient. For this purpose, the cannula can be designed, for example, with a sharp end, a tip, a perforating area or a similar perforating means that can pierce and/or cut through the skin area. Alternatively, however, a separate incision could also be made in a skin section in order to then introduce the cannula.

The device can furthermore have at least one device for setting and/or limiting the depth of implantation. For example, a device of this kind for setting and/or limiting the depth of implantation can comprise a depth abutment. By means of such a device, it is possible at all times to ensure that the depth of implantation is uniform and reproducible in all implantation situations, since the quality of the optical coupling is essentially dependent on the uniformity of the depth of implantation.

The device can furthermore comprise at least one storage tank for receiving the first prepolymer liquid and/or the second prepolymer liquid. Separate or common storage tanks can be provided. Moreover, the device can comprise at least one pressure device for generating an overpressure and/or an underpressure, in order thereby to suck and/or force the first and/or second prepolymer liquid into the cannula.

The device can in particular have at least one admission valve, said admission valve being connected to an auxiliary reservoir. The auxiliary reservoir can, for example, be a saline solution or another kind of auxiliary fluid that can be used, for example, to compensate underpressures inside the storage tank.

The pressure device can, for example, comprise at least one plunger that remains fixed in place during implantation, for example a plunger connected in a fixed manner to the at least one storage tank and/or to the at least one cannula. "Fixed in place during implantation" is to be understood as meaning a device in which, although the rest of the device is designed to move relative to a skin surface for example, the plunger itself is fixed in position relative to the skin surface (for example by means of a suitable abutment on the skin surface). In this way, for example, an underpressure can be generated in a storage tank for the at least one prepolymer during insertion of the cannula, which underpressure is compensated by the auxiliary liquid flowing in. Upon renewed withdrawal of the cannula from the skin area, the storage tank is then moved counter to the fixed plunger, as a result of which an overpressure builds up inside the storage tank. By means of this overpressure, the implant formed in the cannula can then be ejected into the skin area.

This principle can be generalized in terms of the device being designed to insert a cannula into a tissue and then remove it again from the tissue, with a sensor element being automatically pushed out of the cannula into the tissue upon removal of the cannula.

To make it easier in particular to withdraw the cannula from a skin section, the device can furthermore comprise at least one restoring spring element (for example a helical spring, a leaf spring, an elastic element or some other kind of spring element) which is designed to remove the device completely or partially from the body fluid and/or from the body tissue after an implantation movement.

As has been described, the cannula can be designed with a constant or varying cross section. However, it is particularly preferable if the cannula has, at a predefined distance from the tip of the cannula, a constriction (for example a neck and/or a constriction, in particular a conical constriction). Such a constriction can be used to advantage in various ways. In the first instance, such a constriction, for example taking up to 1 percent, up to 10 percent or even up to 20 percent or more of the cross section of the cannula, represents a "predetermined break" in the formation of the sensor element at which, for example, prepolymer solution in the cured or semi-cured state is separated from prepolymer solution which is situated above it and in communication with a storage tank. Upon removal of the cannula from the body tissue, it is highly likely that a tear will occur at this location.

The constriction can also be made use of when removing the implant from the tissue since the sensor element (and if appropriate the surrounding body fluid) can be sucked on via the cannula until the tapering needle or cannula is occluded by the implant. The cannula including the sensor element or implant can then be withdrawn again from the skin. Therefore, the same and/or similar devices can be used both for the implantation and also for the removal of the sensor element from the skin section. The distance between the tip of the cannula and the constriction is therefore preferably substantially equal to the length of the implanted sensor element.

Further details and features of the invention will become evident from the following description of preferred illustrative embodiments in conjunction with the dependent claims. Here, the respective features can be embodied singly or in combination with one another. The invention is not restricted to the illustrative embodiments. The illustrative embodiments are depicted schematically in the figures. The same reference numbers in the individual figures designate identical elements or elements that have an identical function or that correspond in terms of their functions.

DETAILED DESCRIPTION

Figure 1:
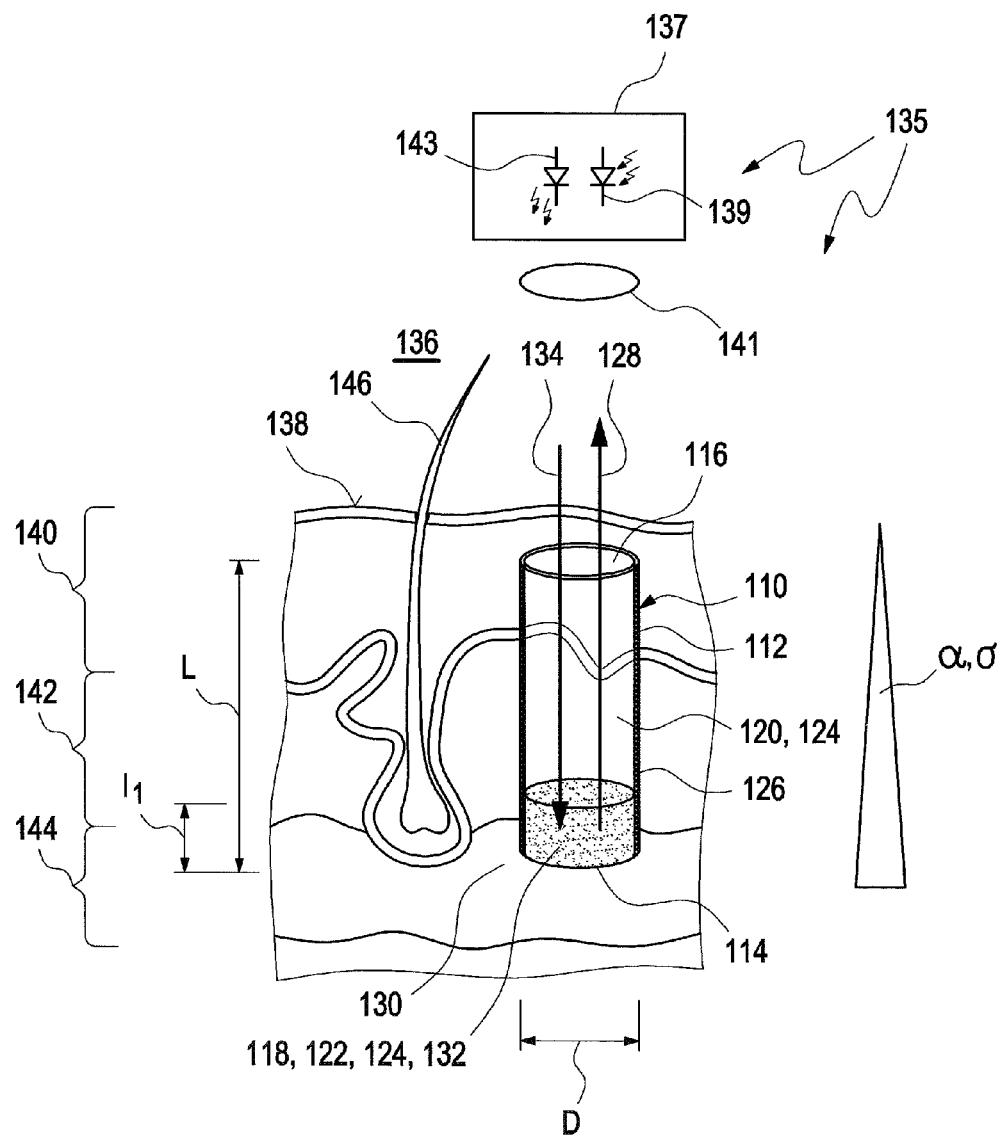
FIG. 1 shows a sensor element according to the invention implanted in body tissue.

In FIG. 1, a sensor element 110 according to the invention is shown in the implanted state. The sensor element 110 has a one-piece shaped body 112 with a sensor end 114 and a coupling end 116. In this illustrative embodiment, the shaped body 112 is designed as a continuous hydrogel shaped body and comprises, for example, the above-described materials. In this example, the shaped body 112 has a substantially cylindrical form, with a diameter D of approximately 200-500 micrometers and an overall length L of approximately 2-5 millimeters. Here, the sensor element 110 is subdivided into a sensor area 118, which in the implanted state points into the interior of the tissue, and a transparent coupling part 120. The sensor area 118 has a length l1 of approximately 500 micrometers. Greater dimensions are disadvantageous in some cases, since the response times of the sensor element 110 then become too long on account of the long diffusion paths. In the sensor area, a sensor material 122 is embedded in a matrix material 124, the matrix material 124 also being contained in the area of the coupling part 120.

The figure also shows that the sensor element 110 can optionally be surrounded by a coating 126, for example a biocompatible coating and/or a coating with an active substance that promotes healing. The coating 126 can, for example, be applied using a layer-by-layer method or a plasma coating method.

The figure also shows that the transparent coupling part 120 serves as a "window" for coupling out an optical signal 128. This optical signal 128 can, for example, comprise light emitted and/or reflected by the sensor material 122, which emitted light can be emitted for example in the form of fluorescent light and/or luminescent light. This optical signal 128 of the sensor material 122 is sensitive to the presence of an analyte in a body tissue 130 surrounding the sensor end 114. Furthermore, in addition to the sensor material 122, the sensor area 118 can also contain a reference material 132 which likewise contributes to the optical signal 128 and can reflect or emit a reference component of this optical signal 128. Furthermore, FIG. 1 depicts an optional excitation beam 134 by means of which, for example, the sensor material 122 and/or the reference material 132 can be specifically excited. The question of whether it is necessary to use an excitation beam 134 of this kind will depend on the nature of the sensor material 122 and/or of the reference material 132 and/or on the optical detection mechanism used to detect the at least one analyte in the body tissue 130 and/or in a body fluid which surrounds the sensor area 118. The coupling part 120 preferably does not serve as an optical waveguide, i.e. no use is made of the wave-conducting properties of structures with different refractive indices, and instead the refractive index in the area of the coupling part 120 is preferably substantially homogeneous. Thus, the coupling part 120 only acts as a "window" for "viewing" the sensor area 118 from the external area 136 outside of the skin surface 138.

It will be seen that the sensor element 110 is preferably implanted into the body tissue 130 in such a way that the coupling end 116 of said sensor element is still arranged below the skin surface 138. The skin surface 138 above the coupling end 116 is preferably already healed again during measurement operation.

As an example of a body tissue 130, the illustrative embodiment in FIG. 1 shows a skin section with an epidermis 140, dermis 142 and subcutis 144, and with a hair 146 being shown for size comparison. Furthermore, the absorption a and the scattering a are plotted symbolically in FIG. 1. Here, it can be seen that the scattering and the absorption are low in the area of the skin surface 138 and increase with increasing depth in the interior of the body tissue 130. It will be noted that the skin section shown is only to be understood as one example of a possible site of implantation, and an implantation can therefore also take place in other types of body tissue 130, for example a tissue within an eye or in other types of body tissue too.

A sensor arrangement 135 according to the invention is also shown in FIG. 1. In addition to the sensor element 110, this sensor arrangement 135 comprises a detection device 137 with at least one optical detector 139. The optical detector 139 is only shown symbolically in FIG. 1 and is here symbolized as a photodiode. However, as has been explained above, a multiplicity of optical detectors and/or additional devices, for example devices for spectral separation of the optical signal 128, can be provided in order to detect the optical signal 128 from the sensor material 122 and/or the reference material 132. The detection device 137 in FIG. 1 is designed for coupling to the coupling end 116 of the sensor element 110, said coupling preferably taking place through the uppermost layers of the body tissue 130. By way of example, the detection device 137 can be placed for this purpose onto the skin surface 138. In FIG. 1, the detection device 137 is optionally designed with additional optical devices 141 which are likewise only shown symbolically and which can, for example, comprise corresponding optics (lenses, objectives, diaphragms or the like).

Furthermore, in the illustrative embodiment shown in FIG. 1, the detection device 137 optionally comprises at least one radiation source 143 for generating the optional excitation beam 134. The radiation source 143 is again shown symbolically as a light-emitting diode, although, as has been described above, a large number of other types of radiation sources can be included.

In addition to the optical device 141, the optical detector 139 and the radiation source 143, it is also possible for the detection device 137 to comprise further components, such as input and output means, energy supplies, data processing devices or the like. For examples of possible configurations, reference is made to the above description.

Figure 2:
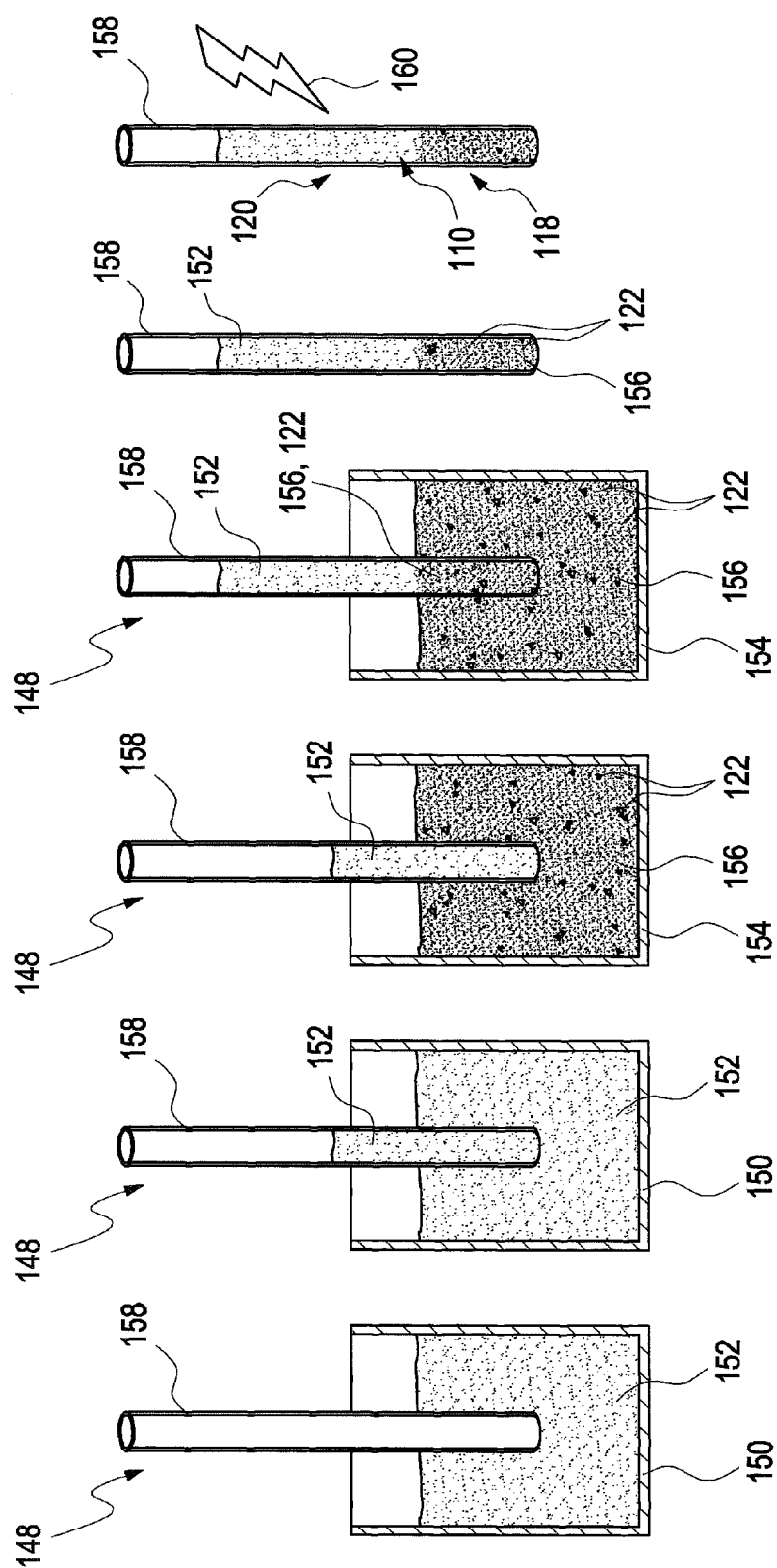
FIGS. 2A-2F show a method according to the invention for producing a sensor element.

FIGS. 2A to 2B are symbolic representations of method steps for producing a sensor element 110, for example a sensor element 110 according to FIG. 1. These figures also show the preferred components of a device 148 according to the invention of a sensor element 110, namely a first storage tank 150 with a first prepolymer liquid 152, a second storage tank 154 with a second prepolymer liquid 156, at least one sensor material 122, which in this illustrative embodiment is mixed into the second prepolymer liquid 156, and a cannula 158. It will be noted that the two storage tanks 150, 154 can also be combined, since the two prepolymer liquids 152, 156 do not necessarily have to be introduced separately into the cannula 158, for example since the introduction of the sensor material 122 can also take place after the introduction of the prepolymer liquid 152, 156 into the cannula 158.

In the depicted embodiment of the method, a layer of the first prepolymer liquid 152 is first sucked from the first storage tank 150 into the cannula 158 (FIGS. 2A and 2B). The cannula 158 is then dipped into the second storage tank 154, and the second prepolymer liquid 156 mixed with the sensor material 122 is sucked in as a second layer (FIGS. 2C and 2D). The first layer of the first prepolymer liquid 152 in the cannula 158 later forms the coupling part 120 of the sensor element, whereas the second layer, comprising the second prepolymer liquid 156 and the sensor material 122, later forms the sensor area 118 (FIG. 2E).

FIG. 2F shows that, in a further method step, the first prepolymer liquid 152 and the second prepolymer liquid 156, with the sensor material 122 contained therein, are finally cured. This curing can be done for example and preferably by means of irradiation with UV light 160, as is shown in FIG. 2F. The curing can in this case comprise a photochemical polymerization or crosslinking. The first prepolymer liquid 152 and the second prepolymer liquid 156 in this case become at least one matrix material 124 and, in the method shown in FIGS. 2A to 2F, in contrast to the sensor element shown in FIG. 1, these matrix materials do not necessarily have to be identical for the sensor area 118 and the coupling part 120.

For the sensor material 122, it is possible in principle to use any desired sensor materials which, by a change in the optical property, react to the presence of the at least one analyte to be detected. From the prior art, for example the prior art described in the introduction, various materials are known which can also be used in the context of the present invention. For example, the sensor material 122 can comprise fluorescein-dextran and rhodamine-ConA. By incubation in an aqueous solution for example, this fluorescein-dextran or rhodamine-ConA can be embedded in alginate particles produced by an atomization method. These alginate particles can additionally be coated, for example by multiple coating with in each case oppositely charged polyelectrolyte solutions. In this way, the alginate particles charged with the sensor material can be surrounded by a polyelectrolyte shell which, for example, prevents outward diffusion of the sensor material. For an example of a production method in which alginate particles of this kind are produced, reference can be made to WO 2005/079970 A1, for example.

A nelfilcon polymer solution, for example, can be used as the first prepolymer liquid 152 and/or as the second prepolymer liquid 156. A mercury-xenon lamp, for example, can be used for the crosslinking by UV light 160, in which case the cannula 158 is preferably designed as a transparent cannula 158.

The curing or crosslinking process which is shown in FIG. 2F, and which in this case is initiated by UV light 160, can take place in different states. First, this curing process, as shown in FIG. 2F, can take place outside a body tissue 130, for example by illuminating the in this case transparent cannula 158 by means of a UV lamp, which can likewise be a component part of the device 148. Alternatively or in addition, the crosslinking or curing can also take place inside the body tissue 130, for example by inserting the cannula 158 into the body tissue 130. For this insertion, the skin surface 138 can be provided with an incision, or the cannula 158 itself can be equipped with a sharp or pointed end by means of which the skin surface 138 can be perforated. The illumination with UV light can then take place in upper tissue layers of the body tissue 130 in which the absorption does not yet assume excessive values, such that the UV light still passes through the body tissue. In this way, a particularly high degree of sterility of the sensor element 110 is ensured, since the latter is as it were generated directly in the body tissue 130. A third possibility, which can in some cases also be combined with the other possibilities, involves the sensor element 110 being crosslinked or cured outside the cannula 158 and outside the body tissue 130 and thereafter being implanted.

Thus, the illustrated device 148 for producing the sensor element 110 not only comprises the storage tanks 150, 154 and the prepolymer liquids 152, 156 and the cannula 158, as described above, but also a UV light source (not shown in FIG. 2F).

Figure 3:
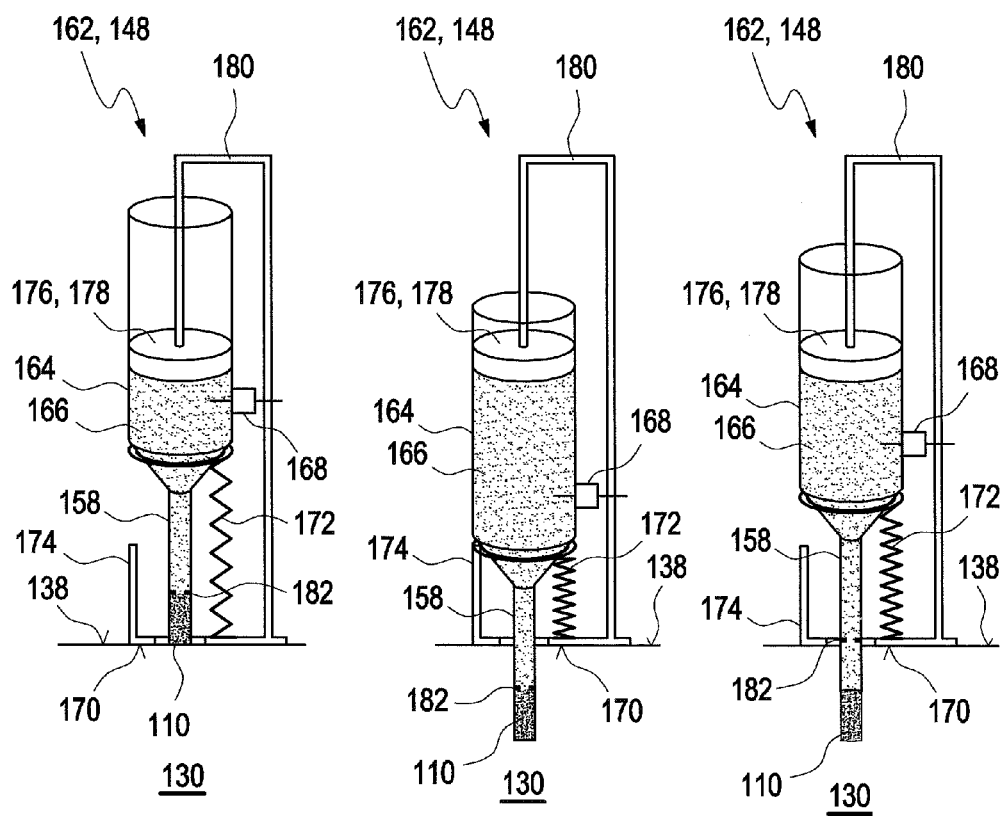
FIGS. 3A-3C show a device according to the invention for producing and implanting a sensor element.

FIGS. 3A-3C show a device 162 for implanting a sensor element 110, which device 162 can also be used at the same time as the device 148 for producing a sensor element. The device 162 again comprises a cannula 158 for perforating a skin surface 138. The device 162 is shown here in a state in which a finished sensor element 110 is already arranged in the cannula 158. This sensor element 110 can in particular be generated inside the cannula 158 according to the method shown in FIGS. 2A-2F. The cannula 158 in this case also acts as an implantation needle.

A storage tank 164 is arranged above the cannula 158. The storage tank 164 can be filled with prepolymer liquid 152, 156 for example, although it can also be filled, after production of the sensor element 110, with an auxiliary liquid 166 as an alternative to or in addition to the prepolymer liquid 152, 156, for example with a saline solution. This auxiliary liquid 166 can, for example, be delivered via an admission valve 168, for example from an auxiliary reservoir (not shown in the figures).

In the illustrative embodiment shown in FIGS. 3A-3C, the device 162 has a wide skin-contacting surface 170 (arranged for example in a ring shape around the cannula 158). This skin-contacting surface 170 is placed onto the skin surface 138. The storage tank 164 and the cannula 158 are inserted into the skin surface 138 relative to this skin-contacting surface 170 (cf. FIG. 3B). In doing so, a spring element 172 is compressed (cf. FIG. 3B). The depth of penetration, and thus the depth of implantation, is set by a stop 174. This stop can be designed, for example, as a depth abutment and thus forms a device for setting the depth of implantation.

The device 162 furthermore comprises a pressure device 176 in the form of a plunger 178. In this illustrative embodiment, the plunger 178 is arranged inside the storage tank 164, although it could also, for example, be connected directly to the cannula 158. The plunger 178 is designed in such a way that it remains fixed in place during the implantation, i.e. does not change its position relative to the skin surface 138. This can be achieved for example, as shown in FIGS. 3A-3C, by means of a strut 180, or by means of another type of device that keeps the distance between the skin-contacting surface 170 and the plunger 178 constant.

As the cannula 158 and storage tank 164 are lowered, a slight underpressure develops in the interior of the storage tank 164 because of the fixed plunger 178. The auxiliary liquid 166, preferably physiological saline solution, flows through the admission valve 168, which can be designed for example as a nonreturn valve, into the interior of the storage tank 164, which in this illustrative embodiment has a sleeve-shaped design.

The stop 174 limits the downward movement. The spring element 172 is tensioned by the downward movement, as a result of which the cannula 158 and the storage tank 164 are forced back up again, i.e. from the skin surface 138. With the nonreturn valve of the admission valve 168 now remaining closed, an overpressure develops inside the storage tank 164 and forces the sensor element 110 out of the tip of the cannula 158 into the body tissue 130. The sensor element 110 now no longer moves relative to the skin surface 138.

During the downward movement of the injector, composed of the cannula 158 and of the storage tank 164, it must be noted that the auxiliary liquid 166 can flow in through the nonreturn valve of the admission valve 168 more easily than the sensor element 110 can move inside the cannula 158. Accordingly, it is advantageous if the cannula 158 narrows towards the top, i.e. towards the storage tank 164, or has a constriction 182 to the inside (for example an overhang, a taper, a projection, a bead or the like), which in both cases has the effect that the sensor element cannot move upwards in the cannula 158.

The device 162 shown in FIGS. 3A-3C can also be used to remove the sensor element 110. For this purpose, the empty cannula 158, which narrows towards the top, for example, or is provided with a constriction 182, is injected over the implanted sensor element. Tissue and implant are sucked onto it by the underpressure generated by the stroke of the plunger 178 (in which process, for example, the valve 168 can be closed in order to maintain the underpressure) until the narrowing cannula 158 is closed by the sensor element 110. Thereafter, the cannula 158 including the sensor element 110 can be withdrawn again from the skin surface 138.

The invention claimed is:

1. Sensor element for detecting at least one analyte in a body fluid or in a body tissue, particularly for determining at least one metabolite concentration in a body fluid, wherein the sensor element comprises an implantable, one-piece shaped body, wherein the shaped body comprises a sensor end and a coupling end, wherein the shaped body comprises, in the area of the sensor end, at least one sensor area, wherein the sensor area comprises at least one sensor material which changes at least one optically measurable property in the presence of the analyte, wherein the shaped body also has at least one optically transparent coupling part, wherein the coupling part is designed to transmit electromagnetic radiation in at least one spectral range between the sensor area and the coupling end, wherein the shaped body has, in the sensor area, at least one optically transparent matrix material, wherein the analyte can at least partially diffuse through the matrix material to the sensor material, wherein the sensor material is embedded in the matrix material, wherein the coupling part has a length between 1 millimeter and 8 millimeters and is formed at least partially by the matrix material, wherein the sensor material is at least partially embedded in the matrix material in microcapsules, wherein the matrix material comprises at least one curable plastic comprising a crosslinkable plastic.

2. Sensor element according to claim 1, wherein the coupling part is substantially free of sensor material and the crosslinkable plastic comprises a biocompatible crosslinkable plastic in cured form.

3. Sensor element according to claim 1, wherein the sensor material is immobilized in the matrix material.

4. Sensor element according to one of the claim 1, wherein the matrix material in the sensor area, in the implanted state of the sensor element, is configured to be in direct contact with the body fluid and/or the body tissue.

5. Sensor element according to claim 1, wherein the coupling part is an elongate coupling part with a substantially homogeneous refractive index.

6. Sensor element according to claim 1, wherein the crosslinkable plastic comprises at least one hydrogel and/or at least one random copolymer.

7. Sensor element according to claim 1, wherein the crosslinkable plastic is produced using at least one of the following materials: a nelfilcon polymer; a crosslinkable polyvinyl acetate or a crosslinkable derivative of the polyvinyl acetate; a crosslinkable polyvinyl alcohol or a crosslinkable derivative of the polyvinyl alcohol; a crosslinkable polymer based on polyethylene glycol, in particular based on at least one of the following polymers: bis(acryloyl) polyethylene glycol, bis(acrylamido) polyethylene glycol, a polyurethane based on polyethylene glycol, a bis- or tris-isocyanate, an acryloyl isocyanate; a crosslinkable polymer based on crosslinkable silicone hydrogel copolymers, in particular based on co-polycondenates of bis(aminodimethyl) siloxanes and/or hydrophilic di- and/or tri-isocyanates and/or acryloyl isocyanates; a telechelic polymer and/or a multivalent hydrophilic polymer.

8. Sensor element according to claim 1, wherein the shaped body is provided completely or partially with a biocompatible coating, a multi-layer coating and/or a plasma coating.

9. Sensor element according to claim 1, wherein the shaped body also comprises at least one active substance that promotes healing.

10. Sensor element according to claim 9, wherein the active substance that promotes healing is arranged in and/or on the shaped body in such a way as to be able to diffuse into the surrounding body tissue.

11. Sensor element according to claim 1, wherein at least one reference material in the form of reference particles is also embedded in the sensor area, and wherein the reference material has at least one optically measurable reference property that does not substantially change in the presence of the analyte.

12. Sensor arrangement comprising at least one sensor element according to claim 1 and at least one optical detector, designed for coupling optically to the coupling end, when the sensor element is implanted in a body tissue, and for measuring the at least one optically measurable property of the sensor material.

13. Method for manufacturing a sensor element for detecting at least one analyte in a body fluid or in a body tissue, the method comprising:
    introducing a first prepolymer liquid with at least one first curable prepolymer for producing an optically transparent coupling part into a cannula;
    introducing a second prepolymer liquid with at least one second curable prepolymer for producing a sensor area into the cannula;
    introducing at least one sensor material into the second prepolymer liquid, wherein the sensor material changes at least one optically measurable property in the presence of the analyte; and
    crosslinking the first prepolymer liquid and the second prepolymer liquid, such that a shaped body with a sensor end and a coupling end is obtained.

14. Method according to claim 13, wherein the crosslinking comprises at least one of the following types of crosslinking: a photochemical crosslinking, or, a thermal crosslinking.

15. Method according to claim 13, wherein the first curable prepolymer and the second curable prepolymer are at least partially chemically identical and comprise a curable matrix material.

16. Method according to claim 13, wherein the shaped body at least partially corresponds, in terms of its outer shape, to the shape of the inner lumen of the cannula.

17. Method according to claim 13, wherein the cannula is at least partially transparent.

18. Method according to claim 13, wherein the first prepolymer liquid and/or the second prepolymer liquid are introduced into the cannula from at least one prepolymer reservoir, by being sucked in by means of an underpressure and/or by being forced in by means of an overpressure.

19. Method according to claim 13, wherein the shaped body is additionally provided with a coating comprises at least one of
    a biocompatible coating, in particular a hydrogel coating;
    a multi-layer coating;
    a coating with at least one active substance that promotes healing; and
    a coating with at least one second sensor material that changes at least one optically measurable property in the presence of the analyte.

20. Method according to claim 19, wherein the coating is applied by means of at least one of the following:
- an immersion method;
- an immersion method with at least one subsequent crosslinking step in order to crosslink the coating; and
- a co-extrusion method by means of a cannula with at least two extrusion lumens, wherein at least a first of the extrusion lumens is used to generate the coating and at least a second of the extrusion lumens is used to generate the coupling part and/or the sensor area.

21. Method according to claim 20, wherein at least one preliminary treatment step is performed prior to the application of the coating to improve the adherence of the coating to the shaped body.

* * * * *